United States Patent
Castellini

(10) Patent No.: US 6,800,478 B2
(45) Date of Patent: Oct. 5, 2004

(54) APPARATUS AND METHOD FOR DETECTING BIOFILM IN THE WATER CONDUITS OF DENTAL UNITS

(75) Inventor: Franco Castellini, Bologna (IT)

(73) Assignee: Castellini, S.p.A., Bologna (IT)

( * ) Notice: Subject to any disclaimer, the term of this patent is extended or adjusted under 35 U.S.C. 154(b) by 0 days.

(21) Appl. No.: 10/004,591

(22) Filed: Dec. 4, 2001

(65) Prior Publication Data

US 2002/0068312 A1 Jun. 6, 2002

(30) Foreign Application Priority Data

Dec. 6, 2000 (IT) .................................. BO2000A0713

(51) Int. Cl.[7] .............................................. C12M 1/34
(52) U.S. Cl. ............................. 435/287.1; 435/287.4; 435/288.7; 433/27
(58) Field of Search ........................... 435/287.1, 287.4, 435/287.9, 288.7, 808; 356/435, 440; 433/25, 27, 28, 80, 82

(56) References Cited

U.S. PATENT DOCUMENTS

| | | | | |
|---|---|---|---|---|
| 4,912,332 A | * | 3/1990 | Siebel et al. | 250/356.1 |
| 5,049,492 A | * | 9/1991 | Sauer et al. | 435/30 |
| 5,246,560 A | | 9/1993 | Nekoksa et al. | |
| 5,285,162 A | * | 2/1994 | Davies | 324/425 |
| 5,349,874 A | * | 9/1994 | Schapira et al. | 73/864 |
| 5,487,981 A | | 1/1996 | Nivens et al. | |
| 5,488,856 A | * | 2/1996 | Dirk | 73/61.62 |
| 5,864,140 A | | 1/1999 | Owens | |
| 5,910,420 A | * | 6/1999 | Tuompo et al. | 435/18 |
| 6,106,771 A | * | 8/2000 | Fitton | 422/14 |
| 6,498,862 B1 | * | 12/2002 | Pierson et al. | 382/133 |

FOREIGN PATENT DOCUMENTS

| | | | | |
|---|---|---|---|---|
| CH | 604 741 | | 9/1978 | |
| DE | 19633808 A1 | * | 2/1998 | C12Q/1/22 |
| EP | 0 531 067 A1 | | 3/1993 | |
| EP | 0 591 927 A1 | | 4/1994 | |
| JP | 11169876 A | * | 6/1999 | C02F/3/06 |
| JP | 2000126781 A | * | 5/2000 | C02F/1/60 |
| WO | WO 9712990 A1 | * | 4/1997 | C12Q/1/04 |

OTHER PUBLICATIONS

European Search Report relating to European Application No. EP 01 83 0728.0–2318, May 14, 2002.

* cited by examiner

Primary Examiner—William H. Beisner
(74) Attorney, Agent, or Firm—Fay, Sharpe, Fagan, Minnich & McKee, LLP

(57) ABSTRACT

An apparatus for detecting biofilm in the water conduits of dental units, especially biofilm adhering to the inside surfaces of the conduits, can be used on a water line equipped with a plurality of conduits for supplying fluids to handpieces and fluid consuming units that use fluid from a main supply or accessory fluids from corresponding independent lines. A portion of one of the conduits is equipped with a system for detecting the presence of the biofilm on the surfaces of the portion itself. The invention also relates to a method for detecting the biofilm. The method comprises the steps of contacting the biofilm attached to surfaces with a reagent substance or fluid; altering the biofilm by the reagent substance or fluid; and detecting the alteration that has taken place in the biofilm using the detecting system.

7 Claims, 2 Drawing Sheets

APPARATUS AND METHOD FOR DETECTING BIOFILM IN THE WATER CONDUITS OF DENTAL UNITS

BACKGROUND OF THE INVENTION

The present invention relates to an apparatus and a method for detecting biofilm in the water conduits of dental units.

One of the most important features of current dental units, and one which has undergone considerable development in recent years, especially in terms of technology and hygiene, is the water and air system. In the dental unit, the water line supplies fluids used by dental equipment and patients (water or physiological saline for tumblers and handpieces), or consumer units (swilling water for the spittoon), while the air line is used for certain items of equipment (air spray handpieces, cooling air and drive air).

As regards hygiene, different protocols have been devised to keep the conduits of the water line at the highest possible level of sterility at all times not only while a patient is being treated but also between patients.

To achieve this, the water line is treated with disinfection/sterilization cycles which bring the dental unit to an adequate level of sterility, although this level can be maintained only for a limited length of time. Indeed, a biofilm soon develops inside the water conduits. The biofilm consists of a colony of micro-organisms permanently attached to the inside surfaces of the conduits and encased in a loosely organized matrix of organic substances (for example, exopolymers, polysaccharides, etc.) excreted by the micro-organisms themselves.

The biofilm protects the bacteria from disinfecting/sterilizing actions and soon begins releasing bacteria into the user fluid. Once established, the biofilm also traps other micro-organisms and allows them to thrive within it.

The disinfectant/sterilizing products currently used (the most common is glutaraldehyde) will eliminate the bacteria in suspension but are unable to attack the biofilm in depth. As a result, it will not be long before the bacteria in the biofilm start multiplying again. Performing disinfection cycles with solvents capable of dissolving the biofilm (for example, strong acids or strong alkalis) is unfeasible because such solvents also corrode the conduits and equipment forming part of the dental unit, not to mention the fact that they are unsuitable on account of their biological incompatibility, which will not be described here.

To overcome this problem, the Applicant has devised and developed a sanitizing method and product designed to remove the biofilm, thus removing the protection and source of nourishment of the micro-organisms to expose them to the biocidal action of disinfectants, and using programmed disinfection/sterilizing cycles normally performed by customary dental units.

After sanitization, however, the dental unit must be checked and monitored not only to ensure that there is no biofilm still attached or suspended in the fluid, for example because the fluid has not been completely drained out of the water line after the sanitizing cycle or because the sanitizing cycle has not been sufficiently effective, but also to keep the hygienic state of the conduits under control to detect biofilm if it develops again so that another sanitizing cycle can be performed.

SUMMARY OF THE INVENTION

Whatever the case, depending on, or irrespective of, the above mentioned sanitizing method, the present invention has for an object to provide an apparatus for detecting biofilm, especially biofilm adhering to the inside surfaces of the water conduits of dental units, the apparatus being extremely accurate, quick to provide information on the hygienic state of the conduits, practical to use and easy to apply to the structure of the dental unit without substantially changing the architecture of the dental unit.

This object is achieved through an apparatus and method for detecting biofilm in the water conduits of dental units, especially biofilm adhering to the inside surfaces of the conduits; the apparatus being applicable to a water line equipped with a plurality of conduits for supplying fluids to handpieces and fluid consuming units that use fluid from a main supply or accessory fluids from corresponding independent lines; a portion of one of the conduits being equipped with means for detecting the presence of the biofilm on the surfaces of the portion itself.

In addition to the apparatus, the invention also provides a method for detecting biofilm comprising the steps of contacting the biofilm attached to surfaces with a reagent substance or fluid; altering the biofilm by the reagent substance or fluid; and detecting the alteration that has taken place in the biofilm using the aforementioned detecting means.

BRIEF DESCRIPTION OF THE DRAWINGS

The technical features of the present invention, in accordance with the above-mentioned aims, are set out in the claims below and the advantages more clearly illustrated in the detailed description which follows, with reference to the accompanying drawings, which illustrate preferred embodiments of the invention without restricting the scope of the inventive concept, and in which:

DESCRIPTION OF THE PREFERRED EMBODIMENTS

Figure 1:
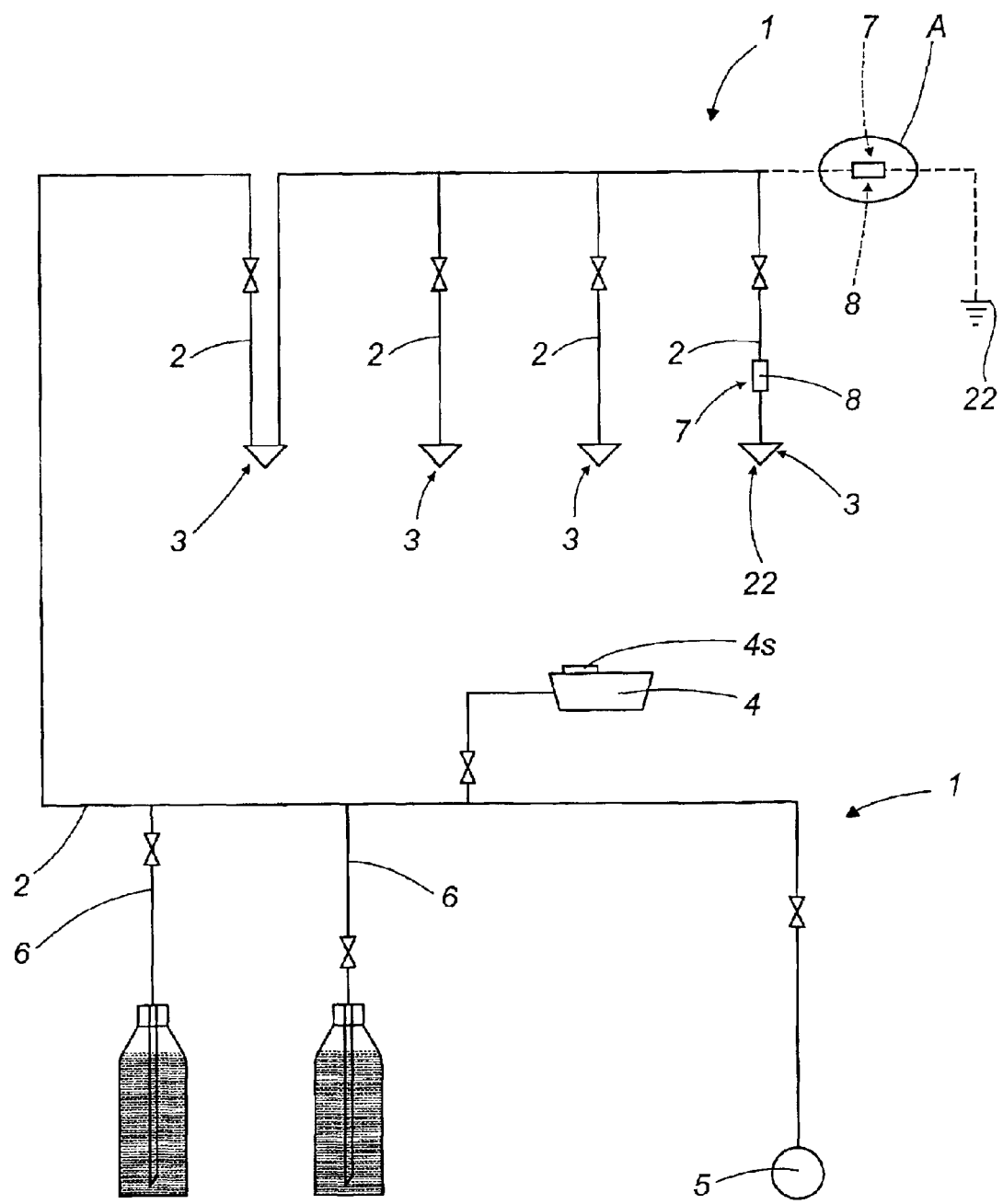
FIG. 1 is a diagram of the water line of a dental unit equipped with the biofilm detecting apparatus according to the present invention.

With reference to the accompanying drawings, in particular FIG. 1, the apparatus according to the invention is used to detect biofilm in the water conduits of dental units.

In particular, the apparatus exposes the biofilm adhering to the inside surfaces of the conduits.

The apparatus is fitted to dental units of the type at least comprising a water line 1 equipped with a plurality of conduits 2 that supply fluids to handpieces 3 (of customary type) and fluid consuming units 4 (such as a spittoon 4s) that use fluid from a main supply 5 (water) or accessory fluids (physiological saline) from corresponding independent lines 6.

A portion 7 of one of the above mentioned conduits 2 is equipped with means 8 for detecting the presence of the biofilm on the surfaces 7a at least of the portion 7 of conduit.

As described in more detail below, the detecting means 8 may of the direct detection type in the conduit portion 7 by reacting with or coloring the biofilm, or of the indirect detection type, but still by reacting with or coloring the biofilm.

Another solution might be to detect changes in the electrical parameters of the biofilm.

In the direct detection solution (see FIG. 2), the detecting means 8 comprise at least the conduit portion 7, which is transparent to allow a direct visual check, and feed means 10 for introducing a reagent or coloring fluid preferably connected to, and acting on, the transparent conduit portion 7. However, the fluid might also be introduced in the entire water line 1 through the means normally used for disinfection/sterilization cycles.

Looking in more detail, the feed means 10 may comprise, for example, a tank 11 containing a suitable reagent or coloring fluid and means 12 for pumping the fluid into the conduit portion 7 or into the whole of the water line 1.

Feed is accomplished (see arrow F1 in FIG. 2) using a valve element 12*v* to open a first connecting channel 12*c* leading into a first end 7*b* of the transparent conduit portion 7. The other end 7*c* of the conduit portion 7 is connected to a second channel 13 (a part of which is shown by a dashed line) for draining out the mixture consisting of the reagent or coloring fluid and the fluid already present in the conduit portion 7 (see arrow F2). The second channel 13 is also controlled by a valve element 13*v*.

Alternatively, the end 7*c* of the conduit portion 7 may be connected to a second channel 13*a* connected directly to the tank 11 and used to recirculate the mixture consisting of the reagent or coloring fluid and the fluid present in the conduit portion 7. In this way, the mixture may be circulated (see arrow F3) for a certain length of time to see whether or not the inside of the conduit portion 7 changes color.

Besides providing the possibility of a direct visual check by the dentist or dental hygienist, the detecting means 8 may comprise optical means 14 located and operating at the transparent conduit portion 7 (see FIG. 2 again), and designed to emit a light beam F before and after the reagent or coloring fluid is introduced so as to reveal a change in the color and/or transparency of the biofilm: for example, by emitting a light beam F whose wavelength is proportional to the coloring of the biofilm.

The optical means 14 may comprise an emitter 15 of the light beam F positioned outside the conduit portion 7, and a control sensor 16 positioned on the opposite side of the conduit portion 7 and designed to receive the light beam F and to check an absorption or transmission coefficient V of the light passing through the conduit portion 7 against a preset reference value V1 defined before introducing the reagent or coloring fluid into the conduit portion 7.

In another embodiment, the optical means 14 may be substituted by means 100 for detecting electrical parameters.

The means 10 may comprise a conductivity sensor 101 positioned inside the conduit portion 7 (see dashed line in FIG. 2 again), whilst the reagent fluid consists of an electrolyte designed to modify one of the electrical parameters of the biofilm, such as conductivity or resistance, detected by the sensor 101 and sent to a comparator unit 102.

The sensor 16 and the comparator unit 102 may be connected to alerting means 17 activated by the sensor 16 through a signal S or Si generated by the sensor 16 or comparator 102 when the value V or V2 of the reading differs from the preset reference value V1 or V3.

Figure 2:
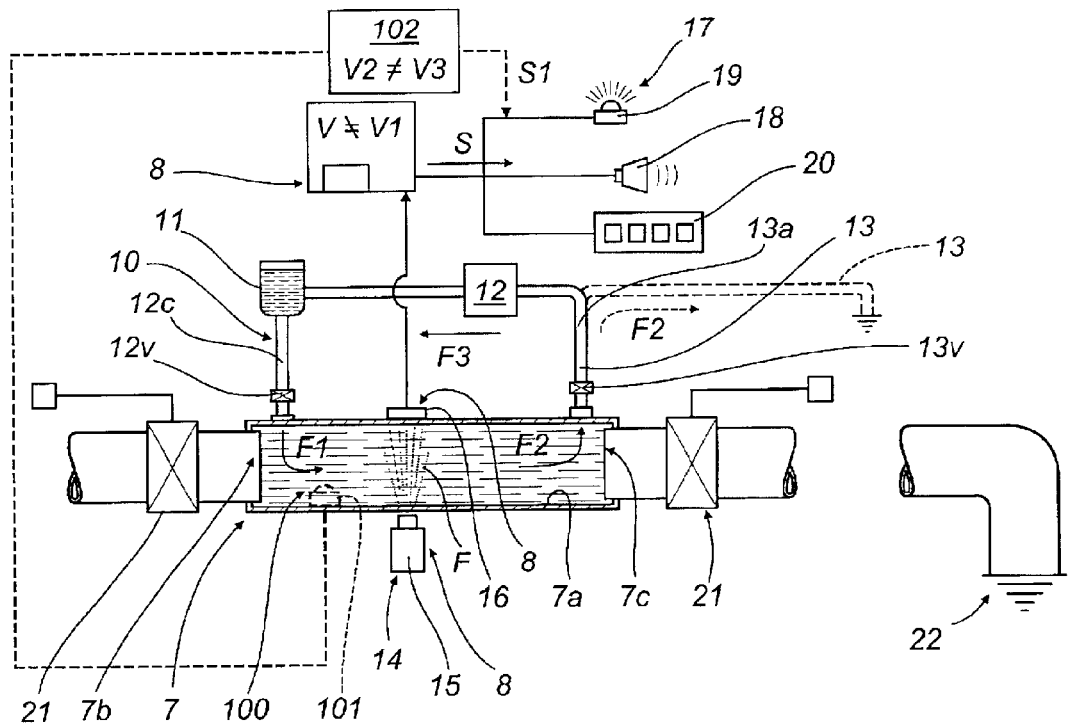
FIG. 2 shows a detail A from FIG. 1, illustrating the detecting apparatus according to the invention in a scaled-up, schematic side view.

As illustrated schematically in FIG. 2, the alerting means 17 may be a device for emitting an audible signal 18 or a warning light 19, or even an alphanumeric display unit 20 to display the value V or V2 of the reading or a message referred to the reading, located on the console of the dental unit, usually made on the handpiece holder.

Structurally, the transparent conduit portion 7 is preferably equipped at the ends of it 7*b* and 7*c* with shutoff valve means 21 designed to isolate the portion 7 from the rest of the water line 1 before the reagent or coloring fluid is introduced.

In addition to this, as shown in FIG. 1, the conduit portion 7 is made in a part of the water line 1 that can be easily inspected by the dentist or dental hygienist. In the preferred embodiment illustrated, the conduit portion 7 may be a part (drawn with a continuous line in FIG. 1) or an extension (drawn with a dashed line) of one of the above mentioned conduits 2 that supply the handpieces 3. In the first case, there may be an independent drain 22 to drain off the fluid mixtures used to check the portion of conduit. In the second case, the end of the handpiece 3 itself may be used to drain off the mixtures.

Figure 3:
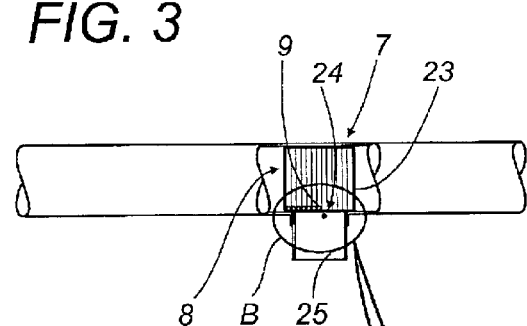
FIG. 3 is a schematic side view of another embodiment of the apparatus according to the invention.
Figure 4:
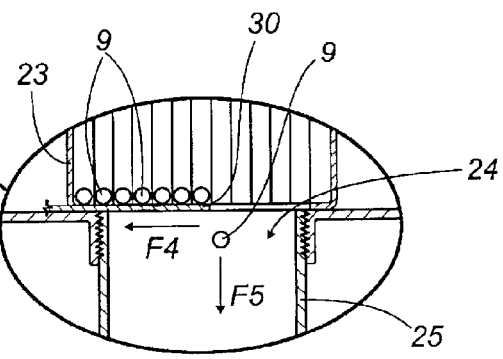
FIG. 4 is a scaled-up view of a detail B from FIG. 3.

FIGS. 3 and 4 illustrate another embodiment of the detecting means 8 of the indirect type.

In this embodiment, the detecting means 8 comprise at least a sample element 9 positioned inside the conduit portion 7 and removable from the conduit portion 7 itself.

The sample element 9 is contacted by the flow of fluid in the dental unit in such a way as to create the same operating conditions as those in the conduit portion 7, thus allowing the biofilm to adhere also to the sample element 9.

Preferably, the conduit portion 7 contains a plurality of the sample elements 9, which may consist of balls made of the same type of material as that of which the conduits of the water line 1 are made.

The sample balls 9 are housed in a cartridge-like container 23 inserted into the conduit portion 7 in such a way as to permit the operating fluid (water) to flow normally through the dental unit.

The container 23 may form an integral part of the conduit portion 7, or, depending on the requirements of the dental surgery, it may be of the disposable type to be used once only to check the water line.

The container 23 may be equipped with a sealed access zone 24 allowing it to be detachably coupled to a sampling cell 25 from which the balls 9 can be taken out one at a time. The cell 25 is preferably of the disposable type.

The cell 25 may be ready-filled with the reagent or coloring fluid or it may be filled at time of use. When biofilm develops, reagent or coloring fluid causes the surface of the ball 9 to change color, thus revealing the presence of the biofilm also in the rest of the water line 1.

As shown in FIG. 4 by way of example, the zone of connection between the container 23 and the cell 25 may consist of a sealed protrusion of the conduit portion 7 (for example sealed and threaded) to retain the cell 25 and a door 30, also sealed, facing the cell 25, operated from the outside and just larger in size than the diameter of a single ball 9: thus, when the door 30 is opened, a single ball 9 is expelled or allowed to drop out of the conduit portion 7 (see arrows F4 and F5).

Further, the use of a multiplicity of balls 9 means that the water line of the dental unit can be checked, once a week, for example, to monitor the presence of the biofilm and so that the water conduits can be sanitized when necessary.

The solution of the indirect type, using sample elements, may also be applied to intermediate parts of the water line, for example, near the aforementioned independent lines 6, where the ball 9 can be conveniently sampled by the dentist or dental hygienist.

The apparatus described above is used to implement a method for detecting biofilm on surfaces 7*a* and 9 in contact with the fluids inside the water line 1 of dental units, the method comprising the following steps:

contacting the biofilm attached to the surfaces (7a in the case of the conduit portion 7, and 9 in the case of the sample ball) with a reagent substance or fluid;

altering the biofilm by the reagent substance or fluid; and detecting the alteration that has taken place in the biofilm using the detecting means 8.

Obviously, as already stated, the reagent substance or fluid may be a coloring agent or an electrolyte.

If the reagent substance is a coloring agent, the step of altering the biofilm is a change in the optical parameters of the biofilm, while the detecting step may consist in simply observing a visually perceptible optical parameter, or it may consist in measuring the optical parameter more precisely and the optical parameter may be the coloring or transparency of the biofilm.

If the reagent substance is an electrolyte, the step of altering the biofilm is a change in the electrical parameters of the biofilm, while the detecting step may consist in measuring these electrical parameters, which, as mentioned earlier, may include the electrical conductivity or resistance of the biofilm.

The apparatus and method described above therefore achieve the aforementioned objects thanks to a structure that is at once highly accurate yet relatively simple and, above all, applicable to the dental unit water lines, including existing ones, easily and at low cost.

The apparatus in particular is extremely important because it allows the conduits of a water line to be safely and quickly observed and checked for the presence of biofilm at any time and at regular intervals. This not only means that the water line can be sanitized whenever necessary but also makes it possible to check whether a treatment carried out on the water line has had the required sterilizing effect.

This in turn means that sanitizing protocols can be optimized (considering that a sanitizing cycle takes a relatively long time) and that the effectiveness of each cycle can be verified after it has been carried out.

The invention described can be subject to modifications and variations without thereby departing from the scope of the inventive concept. Moreover, all the details of the invention may be substituted by technically equivalent elements.

What is claimed is:

1. A dental unit comprising:

a water line equipped with a plurality of conduits that supply fluids to handpieces and fluid consuming units that use fluid from a main supply or accessory fluids from corresponding independent lines; and an apparatus for detecting biofilm in the water conduits, especially biofilm adhering to the inside surfaces of the conduits, the apparatus adapted to dispense a fluid reagent and comprising means for detecting a reaction between the biofilm and the fluid reagent, at least on the surfaces of a conduit portion of one of the conduits, wherein said conduit portion is transparent to allow a direct visual check, and wherein the detecting means, at least in the conduit portion, are of the direct detection type to detect an alteration in the biofilm caused by the fluid and comprise feed means for introducing the reagent or coloring fluid connected to, and acting on, said transparent conduit portion, wherein the feed means comprise a tank containing the reagent or coloring fluid and means for pumping the fluid into the conduit portion through a first connecting channel leading into a first end of the transparent conduit portion, and wherein the other end of the conduit portion is connected to a second channel for draining out the mixture consisting of the reagent or coloring fluid and the fluid already present in the conduit portion.

2. A dental unit comprising:

a water line equipped with a plurality of conduits that supply fluids to handpieces and fluid consuming units that use fluid from a main supply or accessory fluids from corresponding independent lines: and an apparatus for detecting biofilm in the water conduits, especially biofilm adhering to the inside surfaces of the conduits, the apparatus adapted to dispense a fluid reagent and comprising means for detecting a reaction between the biofilm and the fluid reagent, at least on the surfaces of a conduit portion of one of the conduits, wherein said conduit portion is transparent to allow a direct visual check, and wherein the detecting means, at least in the conduit portion, are of the direct detection type to detect an alteration in the biofilm caused by the fluid and comprise feed means for introducing the reagent or coloring fluid connected to, and acting on, said transparent conduit portion, wherein the feed means comprise a tank containing the reagent or coloring fluid and means for pumping the fluid into the conduit portion through a first connecting channel leading into a first end of the transparent conduit portion; the other end of the conduit portion being connected to a second channel connected directly to the tank and used to recirculate the mixture consisting of the reagent or coloring fluid and the fluid present in the conduit portion.

3. A dental unit comprising:

a water line equipped with a plurality of conduits that supply fluids to handpieces and fluid consuming units that use fluid from a main supply or accessory fluids from corresponding independent lines; and an apparatus for detecting biofilm in the water conduits, especially biofilm adhering to the inside surfaces of the conduits the apparatus adapted to dispense a fluid reagent and comprising means for detecting a reaction between the biofilm and the fluid reagent, at least on the surfaces of a conduit portion of one of the conduits.

wherein said conduit portion is transparent to allow a direct visual check, and wherein the detecting means, at least in the conduit portion, are of the direct detection type to detect an alteration in the biofilm caused by the fluid and comprise feed means for introducing the reagent or coloring fluid connected to, and acting on, said transparent conduit portion, and wherein the transparent conduit portion is equipped with shutoff valve means located at the ends of it, designed to isolate the portion from the rest of the water line before the reagent or coloring fluid is introduced.

4. A dental unit comprising:

a water line equipped with a plurality of conduits that supply fluids to handpieces and fluid consuming units that use fluid from a main supply or accessory fluids from corresponding independent lines; and an apparatus for detecting biofilm in the water conduits, especially biofilm adhering to the inside surfaces of the conduits, the apparatus adapted to dispense a fluid reagent and comprising means for detecting a reaction between the biofilm and the fluid reagent, at least on the surfaces of a conduit portion of one of the conduits wherein the conduit portion forms an extension of one of the conduits that supply the handpieces and is equipped with an independent drain.

5. A dental unit comprising:

a water line equipped with a plurality of conduits that supply fluids to handpieces and fluid consuming units that use fluid from a main supply or accessory fluids from corresponding independent lines; and an apparatus for detecting biofilm in the water conduits, especially biofilm adhering to the inside surfaces of the conduits, the apparatus adapted to dispense a fluid reagent and comprising means for detecting a reaction between the biofilm and the fluid reagent, at least on the surfaces of a conduit portion of one of the conduits, wherein the detecting means, at least in the conduit portion, are of the indirect detection type and comprise a plurality of sample elements comprising a plurality of balls made of the same type of material as that of which the conduits of the water line are made, positioned inside the conduit portion and removable from the conduit portion itself; said plurality of sample elements being contacted by the flow of fluid in the dental unit in such a way as to create the same operating conditions as those in the conduit portion, thus allowing the biofilm to adhere also to the plurality of sample elements.

6. The Unit according to claim 5, wherein sample elements are housed in a container and the container has a sealed access zone allowing it to be detachably coupled to a sampling cell from which the balls can be taken out one at a time and which is filled with a biofilm reagent or coloring fluid that causes the surface of the ball to change color perceptibly.

7. The Unit according to claim 6, wherein the sampling cell is of the disposable type.

* * * * *